United States Patent
Hopkins et al.

(10) Patent No.: US 8,045,776 B2
(45) Date of Patent: Oct. 25, 2011

(54) GEOMETRY-DEPENDENT FILTERING IN CT METHOD AND APPARATUS

(75) Inventors: Forrest Frank Hopkins, Cohoes, NY (US); Peter Michael Edic, Albany, NY (US)

(73) Assignee: General Electric Company, Niskayuna, NY (US)

( * ) Notice: Subject to any disclaimer, the term of this patent is extended or adjusted under 35 U.S.C. 154(b) by 1267 days.

(21) Appl. No.: 11/714,306

(22) Filed: Mar. 6, 2007

(65) Prior Publication Data

US 2008/0219532 A1    Sep. 11, 2008

(51) Int. Cl.
 *G06K 9/00*    (2006.01)
(52) U.S. Cl. ........................................................ 382/131
(58) Field of Classification Search .................... 382/131
See application file for complete search history.

(56) References Cited

U.S. PATENT DOCUMENTS

| | | | |
|---|---|---|---|
| 5,311,133 A * | 5/1994 | Dannels | 324/309 |
| 6,324,243 B1 | 11/2001 | Edic et al. | |
| 6,765,983 B2 | 7/2004 | Yan et al. | |
| 6,775,399 B1 * | 8/2004 | Jiang | 382/128 |
| 6,836,570 B2 * | 12/2004 | Young et al. | 382/274 |
| 6,879,656 B2 | 4/2005 | Cesmeli et al. | |
| 6,888,914 B2 | 5/2005 | Edic | |
| 6,901,131 B2 | 5/2005 | Edic et al. | |
| 6,937,689 B2 | 8/2005 | Zhao et al. | |
| 6,956,926 B2 | 10/2005 | Cesmeli et al. | |
| 7,054,405 B2 | 5/2006 | Edic et al. | |
| 7,054,475 B2 | 5/2006 | Edic et al. | |
| 7,065,234 B2 | 6/2006 | Du et al. | |
| 7,082,180 B2 | 7/2006 | Edic et al. | |
| 7,215,732 B2 | 5/2007 | Yin et al. | |
| 7,215,801 B2 | 5/2007 | Bueno et al. | |
| 7,221,728 B2 | 5/2007 | Edic et al. | |
| 7,227,923 B2 | 6/2007 | Edic et al. | |
| 7,298,812 B2 | 11/2007 | Tkaczyk et al. | |
| 7,366,279 B2 | 4/2008 | Edic et al. | |
| 7,376,255 B2 | 5/2008 | De Man et al. | |
| 7,382,852 B2 | 6/2008 | Edic et al. | |
| 2004/0136490 A1 * | 7/2004 | Edic et al. | 378/4 |
| 2005/0031069 A1 | 2/2005 | Kaucic et al. | |
| 2005/0113679 A1 * | 5/2005 | Suryanarayanan et al. | 600/425 |
| 2005/0185753 A1 | 8/2005 | Du et al. | |
| 2005/0286749 A1 | 12/2005 | De Man et al. | |
| 2006/0023832 A1 | 2/2006 | Edic et al. | |
| 2006/0045371 A1 * | 3/2006 | Li | 382/254 |
| 2006/0133564 A1 * | 6/2006 | Langan et al. | 378/8 |
| 2006/0233295 A1 | 10/2006 | Edic et al. | |

(Continued)

OTHER PUBLICATIONS

Laigao M. Chen, Yun Liang, George A. Sandison, and Jonas Rydberg,"Novel method for reducing high-attenuation object artifacts in CT reconstructions," Proc. SPIE 4684, 841 (2002), DOI:10.1117/12.467232.*

(Continued)

*Primary Examiner* — Brian Werner
*Assistant Examiner* — Nirav G Patel
(74) *Attorney, Agent, or Firm* — Fletcher Yoder

(57) ABSTRACT

A method is provided for processing an image. The method comprises identifying one or more contours or surfaces in a two-dimensional or three-dimensional image generated from a set of projection data. The set of projection data is differentially processed based on the identification of those data points that largely define one or more contours or surfaces. An enhanced image set is reconstructed from the set of processed projection data.

29 Claims, 2 Drawing Sheets

U.S. PATENT DOCUMENTS

Figure 1:
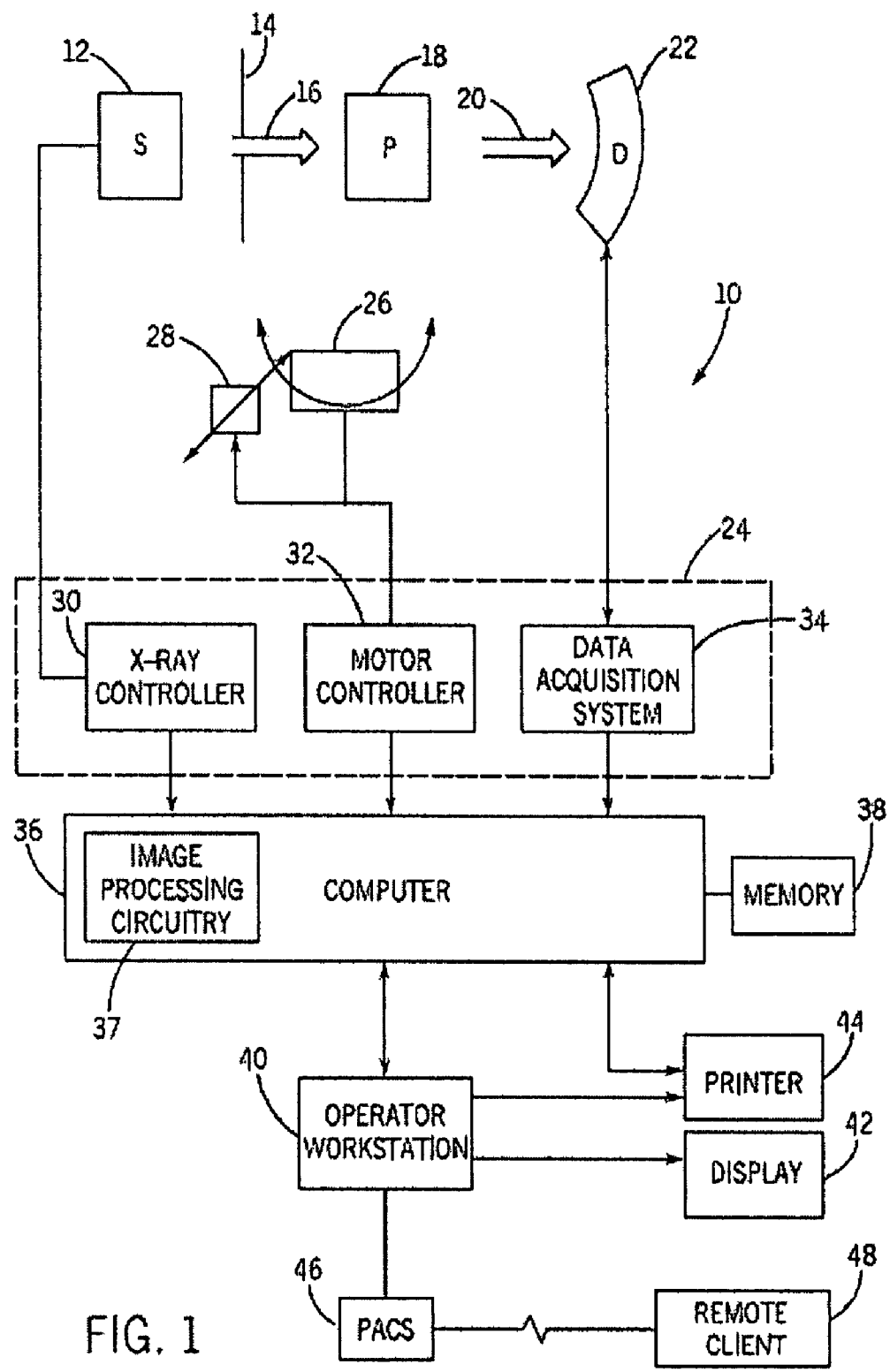

| | | | |
|---|---|---|---|
| 2008/0056432 | A1 | 3/2008 | Pack et al. |
| 2008/0056435 | A1 | 3/2008 | Basu et al. |
| 2008/0056437 | A1 | 3/2008 | Pack et al. |
| 2008/0144959 | A1* | 6/2008 | Rasch et al. .................. 382/260 |

OTHER PUBLICATIONS

Nickoloff El. "Measurement of the PSF for a CT scanner: appropriate wire diameter and pixel size." Phys Med Biol 33: 149-155, 1988.*

Laigao M. Chen, Yun Liang, George A. Sandison, and Jonas Rydberg,"Novel method for reducing high-attenuation object artifacts in CT reconstructions," Proc. SPIE 4684, 841 (2002), DOI:10.1117/12.467232.*

Nickoloff El. "Measurement of the PSF for a CT scanner: appropriate wire diameter and pixel size." Phys Med Biol 33: 149-155, 1988.*

Tahoces, P.G.; Correa, J.; Souto, M.; Gonzalez, C.; Gomez, L.; Vidal, J.J.; , "Enhancement of chest and breast radiographs by automatic spatial filtering," Medical Imaging, IEEE Transactions on , vol. 10, No. 3, pp. 330-335, Sep. 1991.*

Laigao M. Chen, Yun Liang, George A. Sandison, and Jonas Rydberg,"Novel method for reducing high-attenuation object artifacts in CT reconstructions," Proc. SPIE 4684, 841 (2002), DOI:10.1117/12.467232.*

Nickoloff El. "Measurement of the PSF for a CT scanner: appropriate wire diameter and pixel size." Phys Med Biol 33: 149-155, 1988.*

Tahoces, P.G.; Correa, J.; Souto, M.; Gonzalez, C.; Gomez, L.; Vidal, J.J.; , "Enhancement of chest and breast radiographs by automatic spatial filtering," Medical Imaging, IEEE Transactions on , vol. 10, No. 3, pp. 330-335, Sep. 1991.*

Laigao Chen et al., Novel Method for Reducing High-Attenuation Object Artifacts in CT Reconstructions, Proceedings of the Spie, Spie, Bellingham, VA, vol. 4684, Jan. 1, 2002, pp. 841-850.

Oliver Bockenbach et al., Real Time Adaptive Filtering for Digital X-ray Applications, Medical Image Computing and Computer-Assisted Intervention-MIC CAI 2006 Lecture Notes in Computer Science; LNCS, Springer Berlin Heidelberg, BE, vol. 4190, Jan. 1, 2006, pp. 578-587.

* cited by examiner

GEOMETRY-DEPENDENT FILTERING IN CT METHOD AND APPARATUS

BACKGROUND

The present invention generally relates to the field of image reconstruction in computed tomography (CT) systems and more particularly to a method and apparatus for reducing artifacts in image data generated by computed tomography systems.

CT scanners operate by projecting fan-shaped or cone-shaped X-ray beams from an X-ray source. The X-ray source emits X-rays at numerous angular positions relative to an object being imaged, such as a patient, which attenuates the X-ray beams as they pass through the object or patient. The attenuated beams are detected by a set of detector elements, which produce signals representing the intensity of the incident X-ray beams. The signals are processed to produce data representing the line integrals of the attenuation coefficients of the object along the X-ray paths connecting the X-ray source to the detector elements. These signals are typically called "projection data" or just "projections". The individual attenuation values in a given projection are typically referred to as data points. By using reconstruction techniques, such as filtered backprojection, useful images may be formulated from the projections. The images may in turn be associated to form a volume rendering of a region of interest. In a medical context, pathologies, specific physiological regions, or other structures of interest may then be located or identified from the reconstructed images or rendered volume. In non-medical contexts, otherwise inaccessible items or structures, such as items within a bag or package, may be observed and/or studied.

Reconstructed images in CT systems often exhibit a blurring of structures in the direction of the radiation beams that were used to acquire the projection data. Volumetric images obtained with most reconstruction methods exhibit artifacts; such artifacts can be due to high-contrast structures in the imaged volume. These artifacts make image interpretation and visualization steps difficult. The artifacts associated with an imaged structure vary depending on the orientation of the structure with respect to the acquisition geometry and the opacity of different features within the structure, such as long straight edges or areas of high X-ray attenuation. Therefore, the blurring of structures, or edges between structures, may create undesirable image artifacts and inhibit the separation of structures in the reconstruction of the imaged volume.

Different filtering techniques are used during reconstruction of the volumetric images to try to minimize or eliminate artifacts and enhance area definitions that represent features of interest in the three-dimensional structure. A filter is selected for processing the projection data prior to the backprojection. Depending on the filter chosen, either the spatial resolution or contrast sensitivity can be enhanced, at the expense of degrading the other. Contrast sensitivity is a measure of the ability to detect a region in a reconstructed image with a density value that is slightly different from the surrounding background in the presence of noise. For example, an increase in spatial resolution through filtering will result in a decrease in contrast sensitivity, and vice-versa. A further limitation of this approach is the selection of a single filter for the backprojection of all projection data, without regard for changes in features or surfaces throughout the imaged volume. Typically a filter, referred to herein as a standard filter, is used which represents a balance between spatial resolution and contrast sensitivity. An improved filtering technique for dealing with subtle contrast changes between features, i.e. improved contrast sensitivity, without compromising spatial resolution is in certain cases desirable. Alternatively, an improved filtering technique for increasing the spatial resolution for selected regions, without compromising contrast sensitivity, may be desirable.

BRIEF DESCRIPTION

A method for processing an image is provided. The method includes the act of identifying one or more surfaces in a three-dimensional image generated from a set of projection data. The method also includes differentially processing the set of projection data based on the one or more surfaces, and reconstructing an enhanced image from the set of processed projection data.

An image processing system is provided. The image processing system includes data acquisition circuitry configured to receive data from an imaging source. The system also includes image processing circuitry configured to identify one or more surfaces in a three-dimensional image generated from the data, to differentially process data based on the one or more surfaces, and to reconstruct an enhanced image from the data.

Another image processing system is provided. The image processing system includes data acquisition circuitry configured to receive data from an imaging source. The image processing system also includes image processing circuitry configured to reconstruct a first image from the projection data, to identify features in the image, and to dynamically filter the projection data based on the identified features.

DRAWINGS

Figure 2:
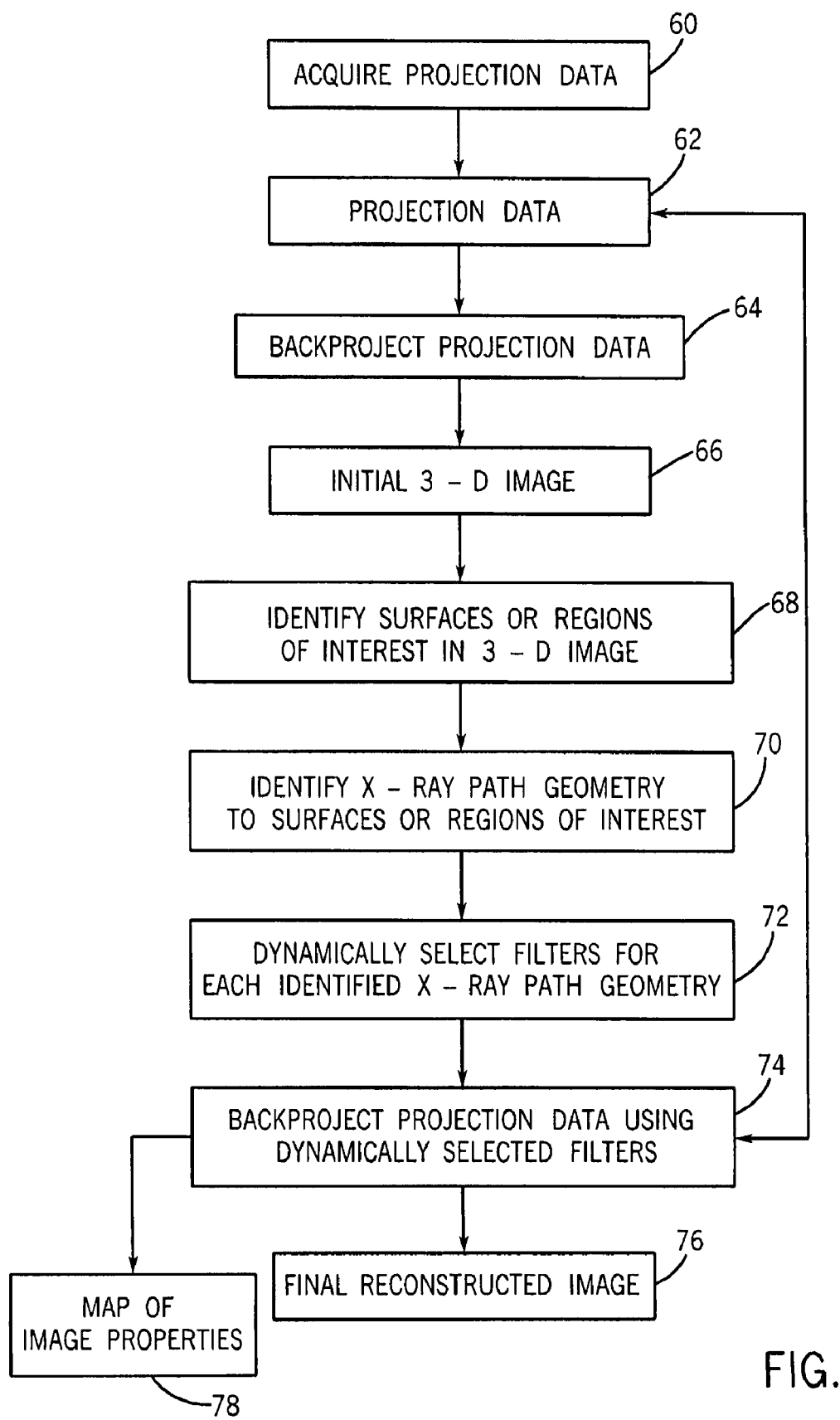

These and other features, aspects, and advantages of the present invention will become better understood when the following detailed description is read with reference to the accompanying drawings in which like characters represent like parts throughout the drawings, wherein:

FIG. 1 is a diagrammatical view of an exemplary imaging system in the form of a CT imaging system for use in producing processed images, in accordance with one aspect of the present technique; and FIG. 2 is a flowchart depicting exemplary actions for reconstructing an image in accordance with the present technique for geometry-dependent filtering in which surfaces are identified from a reconstructed image.

DETAILED DESCRIPTION

FIG. 1 illustrates diagrammatically an imaging system 10 for acquiring and processing image data. In the illustrated embodiment, system 10 is a computed tomography (CT) system designed to acquire X-ray projection data, to reconstruct the projection data into an image, and to process the image data for display and analysis in accordance with the present technique. Though the imaging system 10 is discussed in the context of medical imaging, the techniques and configurations discussed herein are applicable in other non-invasive imaging contexts, such as baggage or package screening. In the embodiment illustrated in FIG. 1, CT imaging system 10 includes a source 12 of X-ray radiation. As discussed in detail herein, the source 12 of X-ray radiation may be a conventional X-ray source, such as an X-ray tube, or a distributed source configured to emit X-rays from different locations along a surface. For example, the X-ray source 12 may include one or more addressable solid-state emitters. Such solid-state emitters may be configured as arrays of field emitters, including one-dimensional arrays, i.e., lines, and two-dimensional arrays.

The X-ray source 12 may be positioned proximate to a collimator 14. The collimator 14 may consist of one or more collimating regions, such as lead or tungsten shutters, for each emission point of the source 12. The collimator 14 typically defines the size and shape of the one or more beams of radiation 16 that pass into a region in which a subject, such as a human patient 18 is positioned. A beam of radiation 16 may be generally fan-shaped or cone-shaped, depending on the configuration of the detector array, discussed below, as well as the desired method of data acquisition. An attenuated portion of the radiation 20 passes through the subject, which provides the attenuation, and impacts a detector array, represented generally at reference numeral 22.

The detector 22 is generally formed by a plurality of detector elements, which detect the X-rays that pass through and around a subject of interest. Each detector element produces an electrical signal that represents the intensity of the X-ray beam incident at the position of the element during the time the beam strikes the detector. Typically, signals are acquired at a variety of angular positions around the subject of interest so that a plurality of radiographic views may be collected. These signals are acquired and processed to reconstruct an image of the features within the subject, as described below.

The X-ray source 12 is controlled by a system controller 24, which furnishes power, focal spot location, control signals and so forth for CT examination sequences. Moreover, the detector 22 is coupled to the system controller 24, which commands acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry and associated memory circuitry. The associated memory circuitry may store programs and routines executed by the system controller, configuration parameters, image data, and so forth. In one embodiment, the system controller 24 may be implemented as all or part of a processor-based system such as a general purpose or application-specific computer system.

In the embodiment illustrated in FIG. 1, system controller 24 may control the movement of a linear positioning subsystem 28 and rotational subsystem 26 via a motor controller 32. In imaging systems 10 in which the source 12 and/or the detector 22 may be rotated, the rotational subsystem 26 may rotate the X-ray source 12, the collimator 14, and/or the detector 22 through one or multiple turns around the patient 18. It should be noted that the rotational subsystem 26 might include a gantry. The linear positioning subsystem 28 enables the patient 18, or more specifically a patient table, to be displaced linearly. Thus, the patient table may be linearly moved within the gantry or within the imaging volume defined by source 12 and/or detector 22 configuration to generate images of particular areas of the patient 18. In embodiments comprising a stationary source 12 and a stationary detector 22, the rotational subsystem 26 may be absent. Similarly, in embodiments in which the source 12 and the detector 22 are configured to provide extended or sufficient coverage along the z-axis, i.e., the axis associated with the main length of the patient 18, the linear positioning subsystem 28 may be absent.

As will be appreciated by those skilled in the art, the source 12 of radiation may be controlled by an X-ray controller 30 disposed within the system controller 24. The X-ray controller 30 may be configured to provide power and timing signals to the X-ray source 12. In addition, in some embodiments the X-ray controller may be configured to selectively activate the X-ray source 12 such that tubes or emitters at different locations within the system 10 may be operated in synchrony or independent of one another.

Further, the system controller 24 may comprise a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a processor-based system, such as a computer 36. Alternatively, in other embodiments, the detector 22 may convert the sampled analog signals to digital signals prior to transmission to the data acquisition system 34.

In the depicted embodiment, the computer 36 is coupled to the system controller 24. The data collected by the data acquisition system 34 may be transmitted to the computer 36 for subsequent processing and reconstruction. For example, the data collected from the detector 22 may undergo pre-processing and calibration at the data acquisition system 34 and/or the computer 36 to produce representations of the line integrals of the attenuation coefficients of the scanned objects. In one embodiment, the computer 34 contains image processing circuitry 37 for processing and filtering the data collected from the detector 22. The processed data, commonly called projections, may then be filtered and backprojected by the image processing circuitry 37 to form an image of the scanned area. The image processing circuitry 37 may apply geometry-dependent filtering to the processed data, in accordance with the present technique, to improve image quality and enhance features or regions of interest. The identification and/or enhancement of features or regions of interest through such geometry-dependent filtering may be referred to as "computer-aided geometry determination." Once reconstructed, the image produced by the system 10 of FIG. 1 reveals an internal region of interest of the patient 18 which may be used for diagnosis, evaluation, and so forth.

The computer 36 may comprise or communicate with a memory 38 that can store data processed by the computer 36, data to be processed by the computer 36, or routines to be executed by the computer 36, such as for processing image data in accordance with the present technique. It should be understood that any type of computer accessible memory device capable of storing the desired amount of data and/or code may be utilized by such an exemplary system 10. Moreover, the memory 38 may comprise one or more memory devices, such as magnetic or optical devices, of similar or different types, which may be local and/or remote to the system 10. The memory 38 may store data, processing parameters, and/or computer programs comprising one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 which may be equipped with a keyboard and/or other input devices. An operator may thereby control the system 10 via the operator workstation 40. Thus, the operator may observe the reconstructed image and other data relevant to the system from computer 36, initiate imaging, select and apply image filters, and so forth. Further, the operator may manually identify features and regions of interest from the reconstructed image or the operator may review features and regions of interest automatically identified and/or enhanced through computer-aided geometry determination as discussed herein. Alternatively, automated detection algorithms may be applied to such enhanced features or regions of interest.

A display 42 coupled to the operator workstation 40 may be utilized to observe the reconstructed image. Additionally, the reconstructed image may be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image data.

One or more operator workstations 40 may be linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Turning now to FIG. 2, a flowchart showing exemplary acts for reconstructing an image in accordance with the present technique is shown. Projection data 62 is acquired (block 60) from the CT system described above, a tomosynthesis system, or other suitable image acquisition system. The projection data 62 may also be acquired from static archives, such as stored data records of previously imaged patients or objects. The projection data 62 is backprojected (block 64) to acquire an initial three-dimensional image 66. Alternatively, the three-dimensional image 66 may have been reconstructed previously, for example from a previously imaged patient or object, and stored as a data record. In such an implementation, the three-dimensional image 66 may simply be provided as an input to the method described herein. From the three-dimensional image 66, surfaces or regions of interest are identified (block 68). The surfaces or regions of interest may represent tissues, organs, or any other physiological features of interest of a patient. In the case of an object other than a patient, surfaces may identify or represent different features, materials, or items that were inside of the object or were otherwise present in the imaging volume.

Once surfaces or regions of interest have been identified, the X-ray path geometries of those X-rays that contribute most significantly to surface or region definitions are identified (block 70). The identified X-ray paths will typically be those paths that are tangential or nearly tangential to the surfaces defining the regions of interest, but any such paths that aid in defining the surface or region of interest may be identified. Once the surfaces and regions of interest and corresponding X-ray path geometries have been identified, filters are dynamically selected on a point-by-point, i.e. X-ray path by X-ray path, basis for each X-ray path geometry (block 72). For example, in one embodiment, the filtration enhances feature characteristics of interest, such as the sharpness of the edge of a linear feature, in a dynamic or point-by-point manner, thereby improving the perceived resolution of the image. In such an embodiment, where sharper definition of long straight edges is desired, the filter is chosen to provide better spatial resolution. For all other X-ray geometries, a filter which represents a balance between resolution and contrast may be used. In one implementation, different filters may be applied within a single projection (or view). For example, regions in the image set that require sharpening will utilize an edge-enhancing filter applied to appropriate areas within a given projection, while, in other areas in the image set where the contrast sensitivity is to be maintained or enhanced, a standard or contrast-enhancing filter will be used. It is important to note that areas in the images affect the selection of filter used for the projection data; hence, the same projection data may be filtered differently depending on the desired effect in regions in the image.

Using the projection data 62 previously acquired, a back-projection is performed on the projection data 62 using the dynamic filter selection (block 74) to produce a final reconstructed image 76. A map of image properties 78 for every surface or region of interest may also be generated from the dynamically filtered backprojected projection data. For example, a map of imaging characteristics pertaining to feature definition, such as the estimated sharpness of edges and/or surface boundaries as determined from a density profile normal to a given surface may be generated. Such a map may be provided as an input to downstream image processing and/or analysis routines, such as computer-aided detection or diagnosis (CAD) routines. This information may be provided as an input to CAD algorithms to aid in the detection, characterization, and identification of specific features.

The exemplary steps in FIG. 2 may be performed by the image processing circuitry 37 of a CT system as shown in FIG. 1. Alternatively, the image processing circuitry may be incorporated in a separate image processing system, independent of an image acquisition system such as a CT system. The exemplary steps in FIG. 2 may be initiated or performed by an operator, through an operator workstation 40 as shown in FIG. 1. Further, the exemplary steps may be performed automatically by routines configured to determine surfaces and/or suitable dynamic filtration, as described above. In such an implementation, an operator may review the results of the automated routines before additional processing or final image reconstruction. Such computer-aided geometry determination algorithms can be a part of image processing circuitry of an image acquisition system, such as a CT system as shown above. Alternatively, such computer-aided geometry determination algorithms may be a part of image processing circuitry in a standalone image processing system, capable of processing images acquired through separate acquisition systems. Further, in an additional embodiment, the computer-aided geometry determination, as described herein, may be provided as part of a highly coupled reconstruction and CAD engine. For example, based upon CAD performance or optimization, the filtering performed by the reconstruction algorithm can be implemented in a geometry-dependent manner, as described herein, to enhance edges or improve contrast resolution in subsequent enhanced images, depending upon the nature of the surfaces or regions of interest. Likewise, CAD routines configured to identify surfaces may be implemented as part of the present process to identify those surfaces within a reconstructed three-dimensional image that are of interest and/or are otherwise subject to dynamic filtration as described above. In these manners, CAD and geometry-dependent filtration and reconstruction may be implemented together to reduce operator intervention and involvement.

While only certain features of the invention have been illustrated and described herein, many modifications and changes will occur to those skilled in the art. For example, in some instances, the object being imaged may be simplistic, i.e. contain a limited number of features. For these cases, analysis of the projection data obtained from the object may be used to select the filters used to enhance edges in the object. Specifically, the projection data can be analyzed to determine regions of rapid transitions in the line integral of the linear attenuation coefficient. These transitions may be utilized to affect the choice of dynamically selected filters used for certain X-ray geometries. In such implementations the local contrast sensitivity of all locations defined by this X-ray geometry will be affected by the choice of filter for the specific X-ray geometry. This effect may be addressed using the exemplary approach outlined in FIG. 2 since the 3D reconstructed image is used to select the filters to be used for a particular X-ray geometry. As mentioned above, one or more filters may be used for the same X-ray geometry since the local projection data affects all image locations along the ray defined by the X-ray geometry. In a second example, although the processing method is described in terms of utilizing three-dimensional images, the process equally applies to two-dimensional imaging techniques where volume surfaces are replaced by image contours. In a third example, these processing methods equally apply to various imaging techniques related to CT, including limited-angle CT and laminography. It is, therefore, to be understood that the appended claims are intended to cover all such modifications and changes as fall within the true spirit of the invention.

The invention claimed is:

1. A method for processing an image, comprising:
identifying one or more surfaces in a three-dimensional image generated from a set of projection data via image processing circuitry of an imaging system;
differentially processing the set of projection data based on the one or more surfaces via image processing circuitry of the imaging system, wherein differentially processing comprises dynamically filtering the set of projection data by applying an edge-enhancing filter to those data points in projection data that correspond to attenuation measurements along the ray paths that contribute to the definition of edge features in the reconstructed image set and applying a contrast-enhancing or standard filter to the other data points in the projection data; and
reconstructing an enhanced image from the set of processed projection data via image processing circuitry of the imaging system.

2. The method of claim 1, wherein reconstructing the enhanced image comprises backprojecting the set of differentially processed projection data.

3. The method of claim 1, comprising acquiring the set of projection data with a computed tomography or a tomosynthesis system.

4. The method of claim 1, wherein identifying the one or more surfaces comprises identifying surfaces associated with physiological or physical features of interest.

5. The method of claim 1, wherein differentially processing comprises dynamically filtering the set of projection data to enhance the edges associated with one or more of the identified surfaces.

6. The method of claim 1, wherein differentially processing comprises applying one or more different filters within a single projection.

7. The method of claim 6, wherein, for each projection, those data points corresponding to ray paths that largely define all of the identified surfaces or a portion of the identified surfaces are filtered using an edge-enhancing filter while other data points in the same projection are filtered using a contrast-enhancing filter or standard filter.

8. The method of claim 6, wherein for each projection, those data points corresponding to ray paths that largely define all of the identified surfaces or a portion of the identified surfaces are filtered using an edge-enhancing filter, while the same data points in the projection corresponding to regions that are not surfaces are filtered using a contrast-enhancing filter or standard filter.

9. The method of claim 1, comprising generating a map of imaging characteristics at all points on all surfaces.

10. The method of claim 9, wherein the imaging characteristics comprise the estimated spatial resolution along density profiles taken normal to the surfaces.

11. An image processing system, comprising:
data acquisition circuitry configured to receive data from an imaging source; and
image processing circuitry configured to identify one or more surfaces in a three-dimensional image generated from the data, to differentially process data based on the one or more surfaces, and to reconstruct an enhanced image from the data, wherein differentially processing comprises applying one or more different filters within a single projection, wherein, for each projection, those data points corresponding to ray paths that largely define all of the identified surfaces or a portion of the identified surfaces are filtered using an edge-enhancing filter while other data points in the same projection are filtered using a contrast-enhancing filter or standard filter.

12. The image processing system of claim 11, wherein the data is a set of projection data.

13. The image processing system of claim 11, wherein reconstructing the enhanced image comprises backprojecting the set of differentially processed projection data.

14. The image processing system of claim 11, comprising wherein the imaging source is a computed tomography or tomosynthesis system.

15. The image processing system of claim 11, wherein identifying the one or more surfaces comprises identifying surfaces associated with physiological or physical features of interest.

16. The image processing system of claim 11, wherein differentially processing comprises dynamically filtering the set of projection data to enhance the edges associated with one or more of the identified surfaces.

17. The image processing system of claim 11, wherein differentially processing comprises dynamically filtering the set of projection data by applying an edge-enhancing filter to those data points in projection data that correspond to attenuation measurements along the ray paths that contribute to the definition of edge features in the reconstructed image set and applying a contrast-enhancing or standard filter to the other data points in the projection data.

18. The image processing system of claim 11, wherein, for each projection, those data points corresponding to ray paths that largely define all of the identified surfaces or a portion of the identified surfaces are filtered using an edge-enhancing filter, while the same data points in the projection corresponding to regions that are not surfaces are filtered using a contrast-enhancing filter or standard filter.

19. The image processing system of claim 11, comprising generating a map of imaging characteristics at all points on all surfaces.

20. The image processing system of claim 19, wherein the imaging characteristics comprise the estimated spatial resolution along density profiles taken normal to the surfaces.

21. An image processing system, comprising:
data acquisition circuitry configured to receive projection data from an imaging source; and image processing circuitry configured to reconstruct a first image from the projection data, to identify features in the first image, and to dynamically filter the projection data based on the identified features, wherein dynamically filtering the projection data comprises applying an edge-enhancing filter to those data points in the projection data that correspond to attenuation measurements along the ray paths that contribute to the definition of edge features in the first image and applying a contrast-enhancing or standard filter to the other data points in the projection data.

22. The image processing system of claim 21, comprising reconstructing a second image from the filtered data.

23. The image processing system of claim 21, wherein the imaging source comprises a volumetric scanner.

24. The image processing system of claim 21, wherein the imaging source comprises a distributed X-ray source.

25. The image processing system of claim 21, comprising image display circuitry configured to display the image.

26. The image processing system of claim 21, wherein the filter is an edge-enhancing filter.

27. The image processing system of claim 21, wherein the filter is a contrast-enhancing filter.

28. The image processing system of claim 21, wherein the features are surfaces.

29. The image processing system of claim 21, wherein the features are contours.

* * * * *